United States Patent [19]

LeGrow

[11] Patent Number: 5,403,402
[45] Date of Patent: Apr. 4, 1995

[54] METHOD OF REMOVING COATING FROM SURFACES

[75] Inventor: Gary E. LeGrow, Midland, Mich.

[73] Assignee: Dow Corning Corporation, Midland, Mich.

[21] Appl. No.: 179,053

[22] Filed: Jan. 7, 1994

[51] Int. Cl.$^6$ ................................................ B08B 7/00
[52] U.S. Cl. .................... 134/38; 252/174.15; 252/174.21; 252/DIG. 5; 252/DIG. 8
[58] Field of Search ...................... 134/38; 252/174.15, 252/174.21, DIG. 5, DIG. 8

[56] References Cited

U.S. PATENT DOCUMENTS

| | | | |
|---|---|---|---|
| 4,342,742 | 8/1992 | Sebag et al. | 252/174.15 |
| 4,501,682 | 2/1985 | Goodman et al. | 252/174.15 |
| 5,334,331 | 8/1994 | Fusiak | 252/542 |

*Primary Examiner*—Melvyn J. Andrews
*Assistant Examiner*—Zeinab El-Arini
*Attorney, Agent, or Firm*—James L. DeCesare

[57] ABSTRACT

Composition and method of removing a coating painted on a surface. The method involves applying to the surface an acetone based composition containing an organosilicon compound, rubbing the acetone based composition into the surface, and removing from the surface the painted coating and the acetone based composition. The composition is a mixture of 1 to 75 percent by weight of acetone; 1 to 10 percent by weight of water; and 1 to 20 percent by weight of a volatile silicone fluid. The volatile silicone fluid having a vapor pressure of less than 0.10 mm Hg.

8 Claims, No Drawings

METHOD OF REMOVING COATING FROM SURFACES

BACKGROUND OF THE INVENTION

This invention is directed to the removal of paint such as enamels and lacquers from organic and inorganic surfaces, including the removal of nail polish from human or animal fingernails and toenails.

The problem to be solved according to this invention is the formulation of VOC compliant compositions for use in the removal of paint.

American air pollution regulations limit the amount of organic solvents that can be discharged into the atmosphere. The term used for solvents is "volatile organic compounds" (VOC). A volatile organic compound (VOC) is defined as any compound of carbon that has a vapor pressure greater than 0.10 millimeter of mercury at a temperature of twenty degrees Centigrade and a pressure of 760 millimeters mercury.

"Volatile organic content" has been defined as the amount of volatile organic compounds (VOC) liberated from a coating as determined by ASTM D3690 and EPA Reference Method 24, which are standard industrial tests. Under the definition, a volatile organic compound is any compound which enters the atmosphere and photochemically reacts in the atmosphere with nitrogen oxides to reduce ozone and form photochemical smog.

Reduction of VOC has been mandated in several American states, and regulations in the state of California, for example, require less than about 180 grams of volatiles per liter of product to enter the atmosphere. This can be determined by baking ten grams of a product in an oven at one hundred-ten degrees Centigrade for one hour. The amount of solids which remain is subtracted from the total of the ten grams which was tested. Calculations are based on the weight of the volatiles that have evaporated, which is reported as grams per liter.

The United States federal Environmental Protection Agency (EPA) has identified many volatile organic compounds present in consumer products such as common solvents ethanol, isopropyl alcohol, kerosene, and propylene glycol; and hydrocarbon solvents such as isobutane, butane, and propane, which are often employed as propellants in industrial and consumer products.

Some American states, including California under the auspices of the California Air Regulation Board (CARB), have proposed standards which would limit and reduce the amount of volatile organic compounds (VOC) permitted in various consumer products, such as chemically formulated products used by household and institutional consumers. These regulations cover products such as detergents; cleaning compounds; polishes; floor products; cosmetics; personal care products; home, lawn and garden products; disinfectants; sanitizers; and automotive specialty products.

These CARB type standards would effect such widely used consumer products as shaving lather, hairspray, shampoos, colognes, perfumes, aftershave, deodorants, antiperspirants, suntan preparations, lotions, breath fresheners, and room deodorants.

Thus, the problem of legal compliance and the need for new and novel formulations and techniques for reducing organic emissions, should be more than apparent.

SUMMARY OF THE INVENTION

The problem is solved in accordance with the present invention by formulating paint removal compositions with one or more of certain volatile cyclic or volatile linear silicones. These volatile silicones have a vapor pressure below 0.10 mm Hg at twenty degrees Centigrade and hence are not a VOC.

Thus, the object of the present invention is to provide a paint remover which includes as an ingredient thereof, a volatile short chain linear or cyclic silicone fluid having in its molecule methyl groups and either (i) phenyl groups or (ii) alkyl groups containing up to twelve carbon atoms but preferably six, seven, or eight carbon atoms.

The paint remover meets the various regulations mandated by American Federal, State, and Local environmental regulations, on the use of volatile organic compounds (VOC) in industrial products and consumer oriented personal care products, and provides the solution to the problem of being in full compliance with American air pollution regulations.

These and other features, objects, and advantages of the present invention will become more apparent from a consideration of the following detailed description thereof.

DETAILED DESCRIPTION OF THE INVENTION

A nail polish remover is used to remove traces of prior nail lacquer coatings or residues from soap and hand creams, before a new nail lacquer is applied to the fingernails or toenails. The main and major ingredient of most nail polish removers is acetone. While quantities of acetone in excess of about ninety percent by weight have been used in anhydrous nail polish removers of the past, the maximum acetone content now mandated by new and emerging environmental regulations is seventy-five (75) percent by weight.

Nonsmear nail polish removers depend upon the presence of water in the mixture. These aqueous mixtures contain at the most about ten (10) percent by weight of water, since the presence of water increases the time required for removing the nail lacquer from the nails.

Because of the environmental limitations on the use of acetone, some suitable solvent replacement must now be included in both anhydrous and aqueous nail polish removers.

According to this invention, the solvent replacement for acetone is an organosilicon compound selected from the group consisting of (i) a volatile short chain linear silicone fluid having in its molecule only methyl groups, (ii) a volatile cyclic silicone fluid having in its molecule only methyl groups, (iii) a volatile short chain linear silicone fluid having in its molecule both methyl groups and phenyl groups, and (iv) a volatile short chain linear silicone fluid having in its molecule both methyl groups and alkyl groups containing up to twelve carbon atoms, but preferably six, seven, or eight carbon atoms.

All of these fluids have a vapor pressure which is less than 0.10 mm Hg, measured at twenty degrees Centigrade and 760 mm pressure, rendering them acceptable under current non-VOC definitions.

One type of volatile silicone in accordance with the present invention is a low viscosity methylsilicone fluid.

The volatile low viscosity methylsilicone fluid corresponds to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methyl silicone fluid.

The volatile low viscosity methylsilicone fluid contains dimethylsiloxane units and optionally trimethylsiloxane units. Preferably, the methylsilicone fluid has a viscosity of less than about ten centistokes.

Representative compounds are cyclopolysiloxane compounds of the general formula $[(CH_3)_2SiO]_x$, and linear siloxane compounds of the general formula $(CH_3)_3SiO[(CH_3)_2SiO]_ySi(CH_3)_3$, in which x is an integer having a value of from three to ten, and y is an integer having a value of from zero to about four.

The volatile low viscosity methylsilicones have boiling points generally less than about two hundred-fifty degrees Centigrade, and possess viscosities preferably generally less than about ten centistokes measured at twenty-five degrees Centigrade. Most preferably, the viscosity is 0.65 to 5.0 centistokes. The cyclopolysiloxane compounds have been assigned the adopted name "CYCLOMETHICONE" by The Cosmetics, Toiletries and Fragrance Association, Inc., Wash., D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin and nail surfaces, and exhibit enhanced spreadability and ease of rubout when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical. Representative methylsilicone fluids found to be especially useful in accordance with the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$.

These methylsilicone fluids may be used alone, or as mixtures in combinations of two or more. Mixtures of the methylsilicone fluids will result in a volatile material having an evaporating behavior different from any one of the individual methylsilicone fluids.

The methylsilicone fluids and methods for their preparation are known in the art.

Another type of volatile silicone in accordance with the present invention is a volatile short chain linear alkylmethylsilicone fluid. The volatile short chain linear alkylmethylsilicone fluid has the formula:

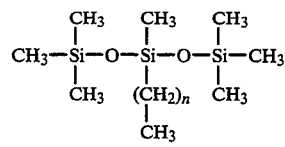

In the above formula, the integer represented by n has a value of five to twelve. Preferably, n has a value of five to eight. Compounds most preferred in terms of this invention are 3-hexyl-1,1,1,3,5,5,5-heptamethyltrisiloxane and 3-octyl-1,1,1,3,5,5,5-heptamethyltrisiloxane. Measured at twenty-five degrees Centigrade, these two preferred compounds have a viscosity of two Centistokes and five Centistokes, respectively.

The alkylmethylsilicones of this invention can be produced by the reaction of a linear siloxane having Si—H functionality in the chain with a slight stoichiometric excess of an alkene $CH_2\!\!=\!\!CHR$ in the presence of a platinum on carbon catalyst. An alkylmethylsiloxane having the structure shown above is produced.

The alkylmethylsilicones of this invention can also be produced by the direct cohydrolysis of methylhydrogen dichlorosilane and trimethyl chlorosilane. The reaction product is contacted with a slight stoichiometric excess of an alkene $CH_2\!\!=\!\!CHR$ in the presence of a platinum on carbon catalyst, and an alkylmethylsiloxane having the structure shown above is produced.

Batch production of the alkylmethylsilicones is conducted by adding the reaction product to a non-agitated suspension of the catalyst in the alkene at about sixty degrees Centigrade. Continuous production of the alkylmethyl polysiloxanes is conducted by pumping a preheated solution of a five percent stoichiometric excess of an alkene $CH_2\!\!=\!\!CHR$ and the reaction product through a packed column containing platinum on carbon catalyst chips. The column will require provision for the removal of heat because of the exothermic nature of the reaction.

The alkylmethylsilicones produced in accordance with the present invention have been found to contain at most about 5 parts per million residual alkene and about 99.95 percent alkylmethylsilicone product. No measurable residual amount of platinum has been detected. The products are otherwise colorless, odorless, clear and stable materials.

Yet another type of volatile silicone in accordance with the present invention is a volatile short chain linear phenylmethylsilicone fluid. The volatile short chain linear phenylmethylsilicone fluid has the formula:

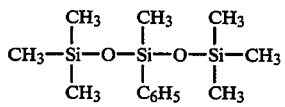

This compound is 3-phenyl-1,1,1,3,5,5,5-heptamethyltrisiloxane.

The most preferred volatile silicone fluids according to the present invention are decamethylcyclopentasiloxane (DMCPS) which has a molecular weight of about 370, a refractive index of 1.40, and the formula $[(Me_2)SiO]_5$; the compound 3-hexyl-1,1,1,3,5,5,5-heptamethyltrisiloxane (HHMTS) which has a molecular weight of about 306, and a refractive index of 1.41; and the compound 3-phenyl-1,1,1,3,5,5,5-heptamethyltrisiloxane (PHMTS) which has a molecular weight of about 298 and a refractive index of 1.45. These compounds will be referred to in the examples and in the table below as DMCPS, HHMTS, and PHMTS, respectively, for the sake of convenience.

The paint remover composition of the invention contains 1 to 75 percent by weight of acetone as the basic and main solvent ingredient; 1 to 10 percent by weight of water, preferably 5.0 to 7.5 percent by weight; 1 to 20 percent by weight of the volatile silicone fluid or a mixture of volatile silicone fluids, but preferably about 15 to 20 percent by weight of the volatile silicone fluid or fluid mixture; and other optional adjuvants to 100 percent, such as coloring agents, perfumes and fragrances, viscosity increasing agents, and emollient oils.

Colorants include any of the United States Government Food & Drug Administration (FDA) certified inorganic and organic dyes and lakes such as carmine, iron oxide, mica, titanium dioxide, ultramarine, zinc oxide, bismuth oxychloride; and D & C Blue No. 1, D & C Orange No. 5, D & C Red No. 6 Aluminum Lake, D & C Red No. 7 Calcium Lake, D & C Green No. 8, D & C Red No. 17, FD & C Blue No. 1, FD & C Red No. 3, FD & C Yellow No. 6, External D & C Violet No. 2, which are the CTFA adopted names of The Cosmetic, Toiletry, and Fragrance Association, Washington, D.C.

Emollient oils which can be employed in the present invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl, stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; hydrocarbons such as petrolatum and squalane.

Fragrances which may be used include natural products such as ambergris, benzoin, civet, clove, leaf oil, jasmine, mateé, mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Thickening agents which may be used include polyacrylates; sodium alignate; gum arabic; guar gum; carboxyvinyl polymers; cellulose derivatives such as methylcellulose, ethyl cellulose, hydroxypropyl methylcellulose, hydroxyethyl cellulose, hydroxypropyl cellulose, and carboxymethyl cellulose; starch and starch derivatives such as hydroxyethylamylose and starch amylose; polyvinyl alcohol; locust bean gum; vegetable gums; magnesium aluminum silicate such as Veegum, a tradename of R. T. Vanderbilt Company, Incorporated, Norwalk, Conn.; saccharide and saccharide derivatives such as fructose, glucose, and PEG-120 methyl glucose dioleate; and the various organically modified montmorillonite clays sold under the trademark BENTONE® by Rheox Incorporated, Highstown, N.J., such as BENTONE®38.

The paint remover compositions are prepared by simply mixing the various components together. The paint remover compositions are used by applying the composition to the surface to be cleaned, rubbing the composition into the surface with cotton or paper towels until the surface below the coating can be seen, and then wiping the surface clean of the coating and the paint remover composition.

The invention will be further illustrated in more detail in the following examples and tables.

EXAMPLE I

Six (6) paint remover compositions were prepared by mixing together acetone, water, and a volatile silicone fluid. These six compositions are illustrated in Table I which shows the proportions of water and volatile silicone in each paint remover. Each of the paint remover compositions in Table 1 contained seventy-five percent by weight of acetone, which is the maximum acetone content permitted under new and emerging VOC constraints and targets in America. The remainder of the paint removal composition consisted of water and the volatile silicone in the amounts indicated in Table I.

TABLE I

| Composition | Water (%) | DMCPS (%) | HHMTS (%) | PHMTS (%) |
|---|---|---|---|---|
| 1 | 7.5 | 17.5 | — | — |
| 2 | 7.5 | 15.0 | 2.5 | — |
| 3 | 7.5 | 15.0 | — | 2.5 |
| 4 | 5.0 | 20.0 | — | — |
| 5 | 5.0 | 15.0 | 5.0 | — |
| 6 | 5.0 | 15.0 | — | 5.0 |

The six (6) paint remover compositions shown in Table I were evaluated as paint removers. Two paints were employed. One paint was a consumer grade commercially available nail polish enamel which was removed from the human fingernails of volunteers. The volunteers evaluated the paint remover compositions for ease of removal, appearance and feel of the nail surface, following the removal of the coating from the nail surface. The other paint evaluated was a non-cross-linked automotive acrylic enamel which was removed from a primed steel surface. It was evaluated for ease of removal.

EXAMPLE III

The six (6) paint remover compositions shown in Table I were evaluated as paint removers by rubbing the coated surfaces in a transverse linear motion with "Q-TIPS" until the substrate below the coated surface could seen with the naked eye. In the case of the nail polish enamel, the entire nail surface was cleaned free of enamel and then inspected for appearance and feel after the elapse of about five minutes.

Based upon the evaluations of both surfaces, Compositions 5 and 6 provided the best results, although the other four compositions functioned adequately as paint removers. Compositions 2, 3, 5, and 6, showed no whitening of the nail surface for the volunteers who had flexible nails. With compositions 5 and 6, nail surfaces felt smooth and had the best appearance. Composition 6 provided nail surface that were shiny.

Other variations and modifications may be made in the compounds, compositions, and methods, described herein without departing from the essential features and concepts of the present invention.

The forms of the invention described herein are exemplary only and are not intended as limitations on the scope of the invention as defined in the appended claims.

That which is claimed is:

1. A method of removing a coating painted on a surface comprising applying to the surface an acetone based composition containing an organosilicon compound; rubbing the acetone based composition into the surface, and removing from the surface the painted coating and the acetone based composition, the composition being a mixture of 1 to 75 percent by weight of acetone; 1 to 10 percent by weight of water; and 1 to 20 percent by weight of a volatile silicone fluid; the volatile silicone fluid having a vapor pressure of less than 0.10 mm Hg; the volatile silicone fluid being selected from the group consisting of decamethylcyclopentasiloxane, 3-hexyl-1,1,1,3,5,5,5-heptamethyltrisiloxane, and 3-phenyl-1,1,1,3,5,5,5-heptamethyltrisiloxane.

2. A method according to claim 1 in which the volatile silicone fluid is a mixture of decamethylcyclopentasiloxane and 3-hexyl-1,1,1,3,5,5,5-heptamethyltrisiloxane.

3. A method according to claim 1 in which the volatile silicone fluid is a mixture of decamethylcyclopentasiloxane and 3-phenyl-1,1,1,3,5,5,5-heptamethyltrisiloxane.

4. A method according to claim 1 in which the surface is a human fingernail and the painted coating is a nail polish lacquer.

5. A method according to claim 1 in which the surface is metal and the painted coating is an acrylic enamel.

6. A method of removing a coating painted on a surface comprising applying to the surface an acetone based composition containing an organosilicon compound; rubbing the acetone based composition into the surface; and removing from the surface the painted coating and the acetone based composition, the composition being a mixture of 1 to 75 percent by weight of acetone; 1 to 10 percent by weight of water; and 1 to 20 percent by weight of a volatile silicone fluid; the volatile silicone fluid having a vapor pressure of less than 0.10 mm Hg; the volatile silicone fluid being a volatile silicone fluid which has a formula selected from the group consisting of

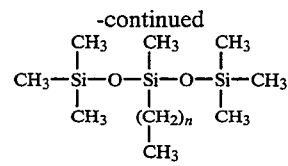

in which y is an integer having a value of from zero to four; and n has a value of five to twelve.

7. A method of removing a coating painted on a surface comprising applying to the surface an acetone based composition containing an organosilicon compound; rubbing the acetone based composition into the surface; and removing from the surface the painted coating and the acetone based composition, the composition being a mixture of 1 to 75 percent by weight of acetone; 1 to 10 percent by weight of water; and 1 to 20 percent by weight of a volatile silicone fluid; the volatile silicone fluid having a vapor pressure of less than 0.10 mm Hg; the volatile silicone fluid being a volatile silicone fluid which has a formula selected from the group consisting of

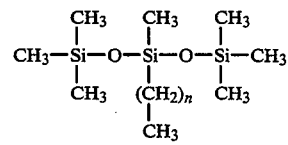

in which n has a value of five to twelve.

8. A method of removing a coating painted on a surface comprising applying to the surface an acetone based composition containing an organosilicon compound, rubbing the acetone based composition into the surface, and removing from the surface the painted coating and the acetone based composition, the composition being a mixture of 1 to 75 percent by weight of acetone; 1 to 10 percent by weight of water; and 1 to 20 percent by weight of a volatile silicone fluid; the volatile silicone fluid having a vapor pressure of less than 0.10 mm Hg; the volatile silicone fluid being selected from the group consisting of a volatile short chain linear silicone fluid having only methyl groups and phenyl groups as substituents on silicon atoms, and a volatile short chain linear silicone fluid having only methyl groups and alkyl groups with six to twelve carbon atoms as substituents on silicon atoms.

* * * * *